United States Patent

Blumenkanz et al.

Patent Number: 5,181,922
Date of Patent: Jan. 26, 1993

[54] METHOD FOR INDENTING THE OCULAR COATS OF AN EYE

[75] Inventors: Mark S. Blumenkanz, Royal Oak, Mich.; Carl Wang, Alameda, Calif.

[73] Assignee: Escalon Ophthalmics, Inc., Skillman, N.J.

[21] Appl. No.: 737,370

[22] Filed: Jul. 29, 1991

[51] Int. Cl.⁵ .............................................. A61B 17/00
[52] U.S. Cl. ...................................... 606/202; 128/898
[58] Field of Search .............. 606/107, 157, 158, 166, 606/201–203, 898, 192; 128/DIG. 25; 600/31; 623/1, 4, 12

[56] References Cited

U.S. PATENT DOCUMENTS

| | | |
|---|---|---|
| 4,299,227 | 11/1981 | Lincoff .............................. 606/107 |
| 4,428,365 | 1/1984 | Hakky ........................ 128/DIG. 25 |
| 4,549,529 | 10/1985 | White ................................ 606/107 |
| 4,634,443 | 1/1987 | Haber .................................. 600/31 |
| 4,708,140 | 11/1987 | Baron ................................ 606/201 |
| 4,773,419 | 9/1988 | Tountas ............................. 606/202 |
| 5,074,869 | 12/1991 | Daicoff ............................. 606/159 |

Primary Examiner—C. Fred Rosenbaum
Assistant Examiner—William Lewis
Attorney, Agent, or Firm—Reising, Ethington, Barnard, Perry & Milton

[57] ABSTRACT

An apparatus and method for indenting the ocular coats for diagnostic and therapeutic purposes. The method includes the steps of (1) gripping the eye at the intra-forniceal bulbar conjunctival surface with an inflatable tubular member having a centripetally expanding surface; and (2) applying pressure to the ocular coats to cause indentation as determined by the controlled filling of the inflatable member.

14 Claims, 5 Drawing Sheets

METHOD FOR INDENTING THE OCULAR COATS OF AN EYE

TECHNICAL FIELD

The present invention relates to an expandable and collapsible apparatus which is useful in various ophthalmological diagnostic and corrective procedures. The present invention is useful in procedures including retinal reattachment, vitrectomy, and cataract surgery.

BACKGROUND OF THE INVENTION

A means for maintaining an indentation of the ocular coats is desirable in many ophthalmic surgical situations. For example, there is need in vitreous surgery (vitrectomy) to tangentially indent the eye wall to access removal of the peripheral vitreous. In cataract surgery, there is a need or desire to soften the eye prior to incision to reduce the risk of unexpected vitreous loss or expulsive hemorrhage. Further, as well documented in the art, it is desirable to create a scleral depression beneath a peripheral retinal break in a detached retina during a reattachment procedure.

More specifically, the retina is a light sensitive tissue covering the internal surface of the posterior ocular coats. It immediately overlies the retinal pigment epithelium and choroid which are responsible for providing nutrient exchange and temperature regulation to the retina. The retina itself contains light and color sensitive elements termed rods and cones which transmit this information to the brain via interconnecting neural elements including the optic nerve. In the brain, as well as in the retina to a lesser extent, the visual information which has been converted to electrochemical information is further processed and integrated resulting in the phenomenon of sight. Any structural or functional abnormality in this system, whether it be in the light refracting surfaces proximal to the retina, the retina itself, the optic nerve, or the visual centers of the brain may cause vision loss or blindness.

The retina is the most critical element in the circuitry since it contains the light sensitive elements (rods and cones). This process termed phototransduction comes about when light energy (photons) are absorbed by a photoactive chemical in the outer portions of the rods and cones which then undergoes a chemical conformational change. This results in the generation of an electrical current which is propagated along the neural portions of the retina to the optic nerve and subsequently to the visual centers of the brain. In order for this light-bleached photoactive chemical to be regenerated to a form capable of receiving further light information, it must receive nutrients including critical products of vitamin A metabolism from the pigment epithelium to which it is normally intimately apposed (1).

The apposition between the retinal pigment epithelium (RPE) and the photoreceptors can be lost as a result of several different pathologic disease processes. Under normal circumstances, the adhesion between the RPE and retina is tenuously maintained by various active metabolic pumps and other concentration gradients including osmotic and oncotic pressure. These depend upon the health and vitality of the individual. Certain diseases or drugs may interfere with the viability of these pumps and result in separation or detachment of the retina from the pigment epithelium. The above pathologic process is termed exudative retinal detachment and is sometimes amenable to medical therapy.

In other pathologic instances, a full-thickness defect may develop in the retina, as a result of tractional or atrophic forces within the eye. The fluid portion of the vitreous humor may then travel through the defect toward a hole or tear in the retina and insinuate itself in the potential space between the retina and the pigment epithelium. This is termed rhegmatogenous retinal detachment.

In some instances, this amount of fluid and consequent separation may be quite large and result in total detachment of the retina. Because the retinal photoreceptors are no longer apposed to the pigment epithelium, the visual pigments can no longer be regenerated; the exchange of nutrients between the choroid and outer retina is disrupted, and vision is lost. If the retina can be subsequently and permanently reposed to the pigment epithelium, vision can be restored to a variable degree depending upon the criticality of portions of the retina initially detached and the duration of that detachment (2).

Although the association between retinal detachment and blindness has been established for several centuries, the identification of the retinal hole as the etiologic agent in rhegmatogenous retinal detachment and a method of therapy was first documented by Jules Gonin, a Swiss ophthalmologist in the 1930's (3). Since that time a variety of methods, all dependent upon identification and closure of retinal holes have been described for repair of retinal detachment. Gonin first described the necessity of puncture of the sclera to release subretinal fluid and, thereby, permit re-approximation of the retina to the pigment epithelium. Thermal irritation of the RPE and retina through the ocular coats in the vicinity of the retinal tear was employed to seal the edges of the hole or tear and, thereby, prevent fluid movement again through it from the vitreous.

Subsequent investigators reported on the utility of indenting the ocular coats of the eye with a prosthesis sutured within or on the scleral coats as a means of enhancing closure of the retinal tear. This reduced the possibility of re-accumulation of subretinal fluid in the immediate postoperative period. These prostheses have been composed of various absorbable and nonabsorbable materials and were commonly refereed to as scleral implants or explants, depending upon whether they were applied within, or on the scleral coats respectively. They yield generally comparable surgical results. Custodis first made the observation that if the surgeon produced a sufficiently high scleral indentation beneath the retinal hole, the subretinal fluid would resorb after variable periods of time without need for scleral puncture and manual drainage (4). This phenomenon of spontaneous reabsorption of subretinal fluid is ascribed to the effect of the metabolic and other pumping forces in the pigment epithelium and choroid. As a result of this observation, newer techniques of retinal reattachment have evolved in recent years which rely upon auto-reabsorption of subretinal fluid following retinal hole closure (5).

One technique involves the injection of a small volume of expandable inert gas into the vitreous cavity. This bubble upon reaching a larger size through exchange with soluble blood gases, temporarily seals the retinal hole from the inside (vitreal) surface rather than outside (pigment epithelial) surface. The net (temporary) effect is the same in that the vitreal fluid is prevented from travelling through the retinal break into the subretinal space during the time that the bubble is apposed to the break provided that the surface area of the bubble is greater than the surface area of the break. During this time, the normal pumping mechanism evacuates the subretinal fluid and reapposes the retina to the pigment epithelium. A chorioretinal adhesion is created by thermal means, either prior to the gas injection or subsequent to retinal flattening to prevent subsequent fluid movement through the hole (6). During the time required for the chorioretinal adhesion to mature, the patient's head must be positioned in such a way the bubble is continuously or near continuously apposed to the tear. This technique is effective in between approximately 40 and 70% of instances depending upon the clinical circumstances. Complications reported include failure to reattach the retina, development of new tears, intraocular bleeding, infection, extension of retinal detachment, intraocular scarring, intraocular pressure elevation, and subretinal migration of gas. It is thought to be less effective in eyes that have multiple retinal tears, eyes with retinal tears in the inferior quadrants, near-sighted (myopic) eyes, and eyes that have previously undergone cataract operations.

Another recently developed technique that relies upon the patient's ability to reabsorb subretinal fluid following closure of the retinal hole is the Lincoff balloon buckle as disclosed in U.S. Pat. No. 4,299,277 to Lincoff, issued Nov. 10, 1981. In this technique, a linear catheter with an inflatable tip, analogoust o a Foley catheter is introduced into the episcleral space beneath the retinal tear through a conjunctival incision. The catheter is then inflated with saline, producing a localized indentation or buckling of the sclera beneath the break (7). If the indentation is sufficient to close the retinal tear or on its external surface (RPE), the subretinal fluid resorbs and a thermal chorioretinal adhesion is induced either prior to catheter placement, or subsequent to reabsorption by cryo therapy or laser photocoagulation, respectively. While also effective in selected cases, this technique also has limitations including patients who have multiple tears. The potential complications include failure to reattach the retina, bleeding, infection, ocular scarring, and pain. The patient must also wear a catheter taped to the face for a period of time postoperatively with attendant risks of infection, bleeding, slippage or discomfort.

While both of these techniques have gained some acceptance, both are not generally applicable to all eyes with retinal detachment especially those containing more than two retinal tears. Since the average detached retina contains approximately three retinal tears and many have preexisting conditions including cataract surgery, glaucoma, myopia or other complicating circumstances, the application of both of these techniques remains limited.

Based upon these considerations as well as concerns regarding the effectiveness and potential complications, conventional scleral buckling remains the procedure of choice for retinal reattachment repair in most centers in the United States today. Based upon incidence estimates of approximately 1:10,000 persons in the United States developing a retinal detachment per year, it is thought that more than 25,000 Americans undergo retinal reattachment repair annually. Taking into account other causes of retinal detachment, re-operations, subclinical retinal detachments which may not undergo scleral buckling and other circumstances, the procedure may be applicable to as many as 50,000 persons per year.

SUMMARY OF THE INVENTION

In accordance with the present invention, there is provided a method of indenting the ocular coats of the eye including the steps of gripping the eye about the bulbar intraforniceal conjunctival surface and then applying a pressure around at least a portion of the bulbar conjunctival surface to indent the eye.

The present invention further provides a device for indenting the ocular coats of the eye, the device including gripping means for gripping the eye about the forniceal bulbar conjunctival surface and pressure applying means operatively connected to the gripping means for applying the pressure about at least a portion of the forniceal conjunctival to indent the eye.

FIGURES IN THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
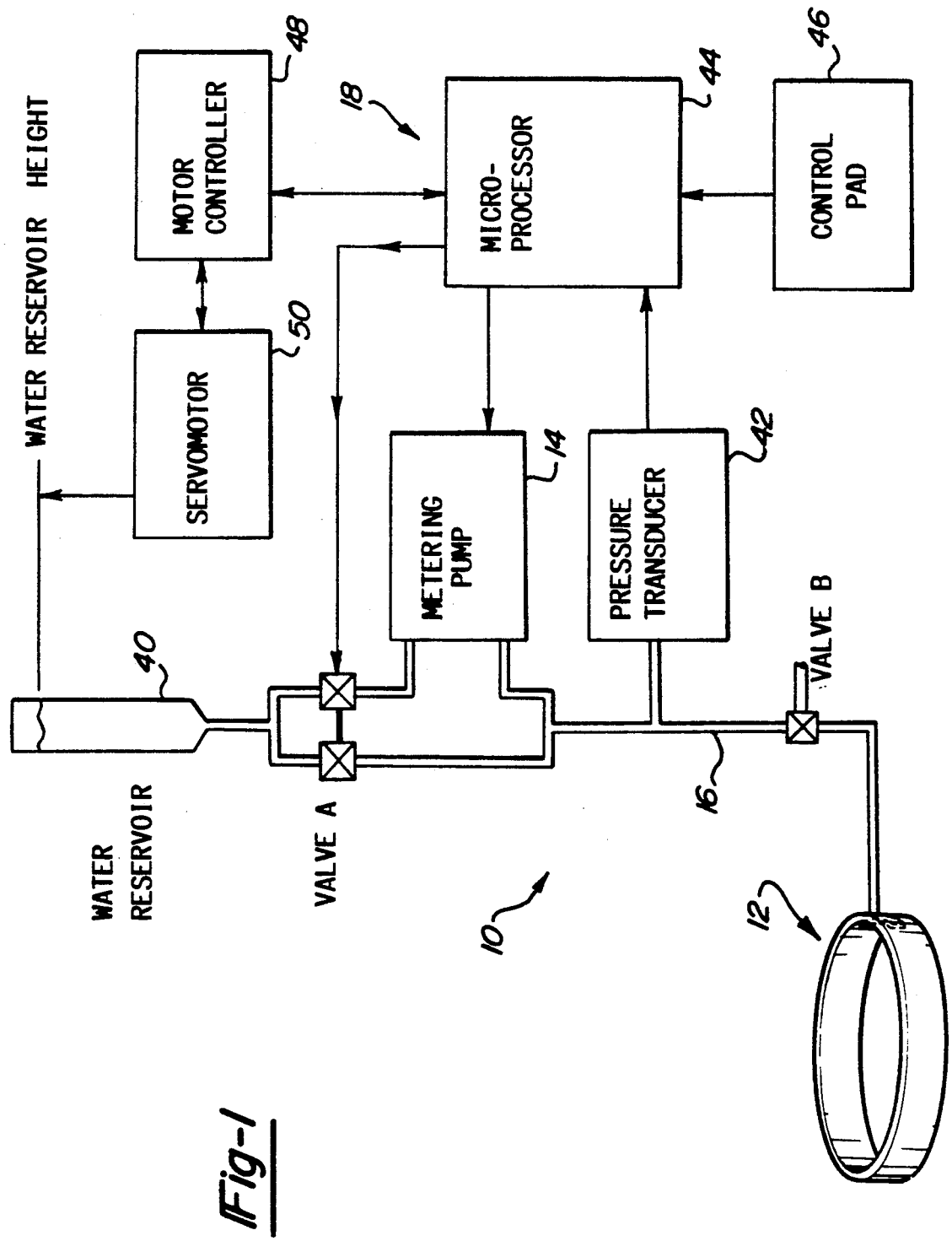
FIG. 1 is schematic representation of a device constructed in accordance with the present invention.

A device for indenting the sclera and choroid coats of an eye is generally shown at 10 in FIG. 1. Most generally, the invention includes means for gripping the eye about the forniceal bulbar conjunctival surface and further includes means for applying pressure about at least a portion of the forniceal conjunctival surface to indent the eye. Unlike prior art devices which required a certain amount of surgery, such as an incision to the eye so as to be operative and placement in a radial direction, the present invention is disposed in the space between the eye and the socket thereby not requiring any surgical procedure. By gripping the eye, the device requires no other tissue or means for maintaining the device in a predisposed position as the device applies a pressure to the eye.

More specifically, and referring to FIG. 1, the device 10 includes a tubular member generally indicated at 12, a pumping mechanism 14, a conduit 16 for conducting fluid to and from the pumping mechanism 14 to the tubular member 12, and a feed-back mechanism generally indicated at 18 for controlling the fluid flow from the pump mechanism 14 to the inflatable tubular member 12.

Figure 2:
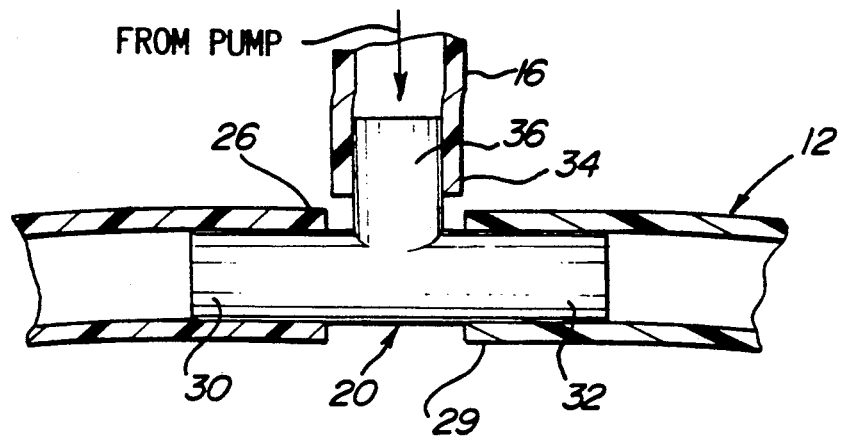
FIG. 2 is an enlarged fragmentary cross sectional view of the junction between the fluid carrying conduit to the inflatable balloon of the present invention.
Figure 3:
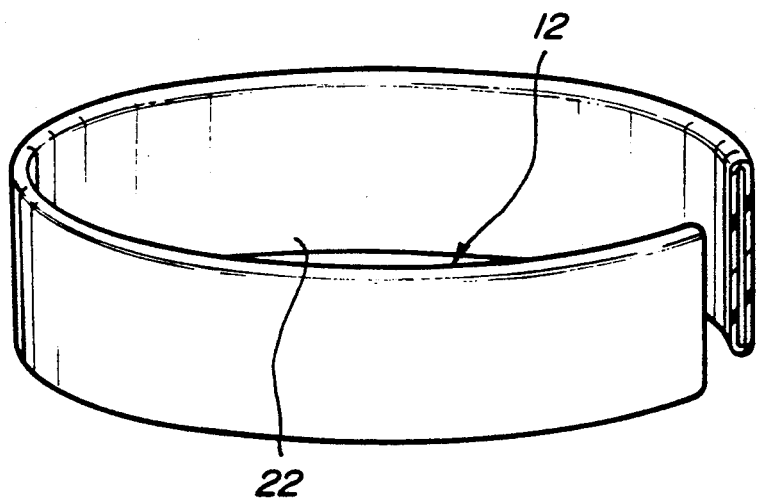
FIG. 3 is a perspective view of the inflatable tubular member, partially in cross section, in the deflated condition.
Figure 4:
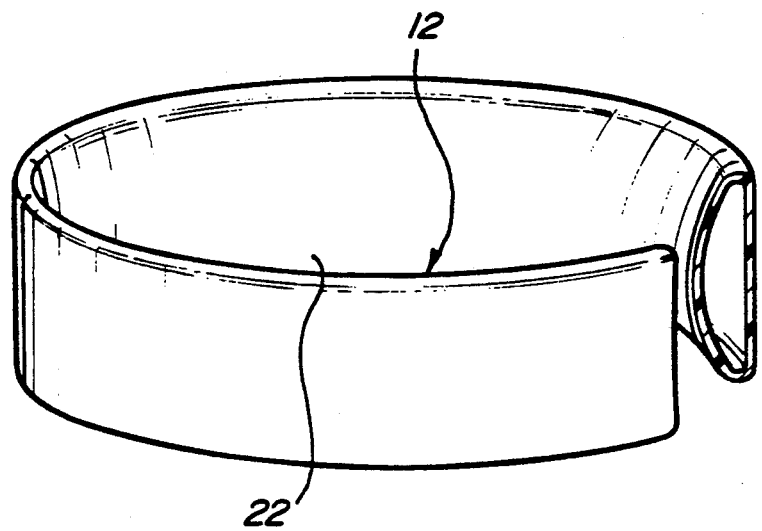
FIG. 4 is a perspective view partially in cross section of the tubular member made in accordance with the present invention which is partially inflated.
Figure 5:
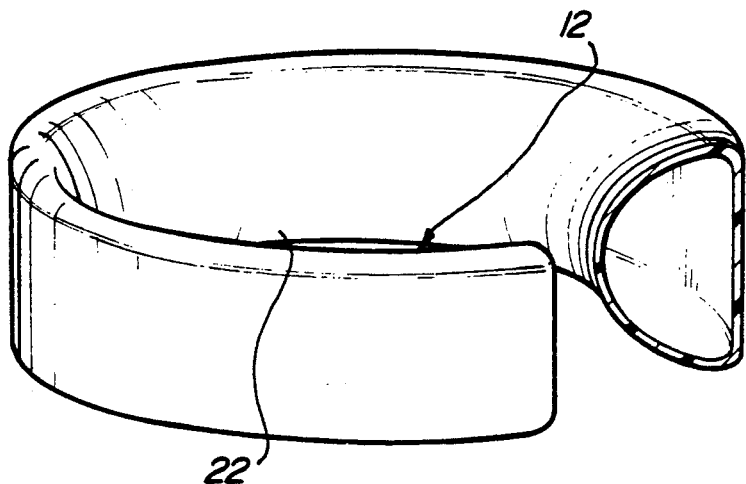
FIG. 5 is a perspective view partially in cross section of the tubular member made in accordance with the present invention which is fully inflated.

Referring more specifically to FIGS. 3 through 5, the inflatable tubular member 12 is an inflatable donut or ring-shape circular catheter composed of an elastic or semi-elastic polymer and/or an inelastic insert containing a valve shown schematically in cross section in FIG. 2 at 20 for the purpose of gas or liquid insufflation. That is, the tubular member 12 can be inflated with either a gas or a liquid as described more specifically below.

The tubular member can be made out of various elastomeric material such as rubber, silicone rubber, latex rubber, plastics, nylon and cellophane.

Figure 6:
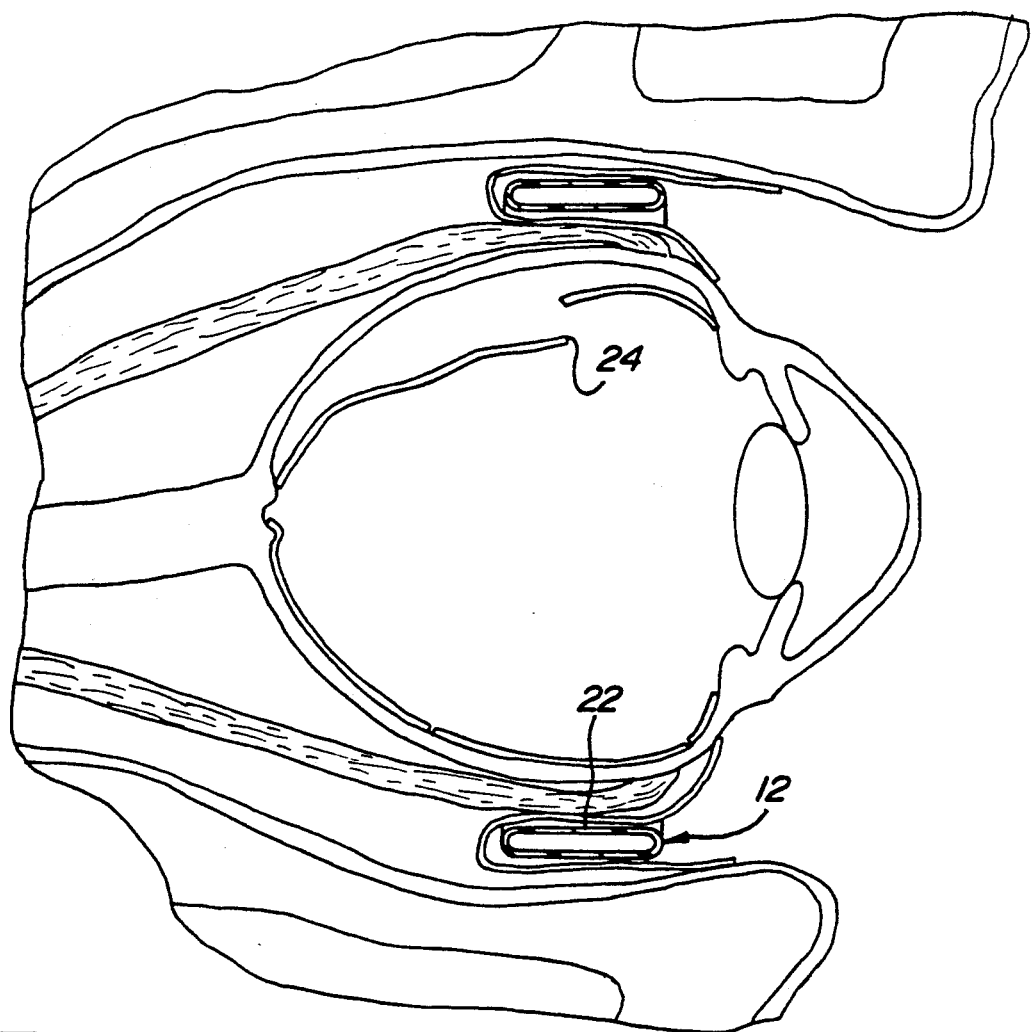
FIG. 6 shows a cross sectional view of the unexpended tubular member of the present invention and the eye shortly after an introduction to the eye of the device.
Figure 7:
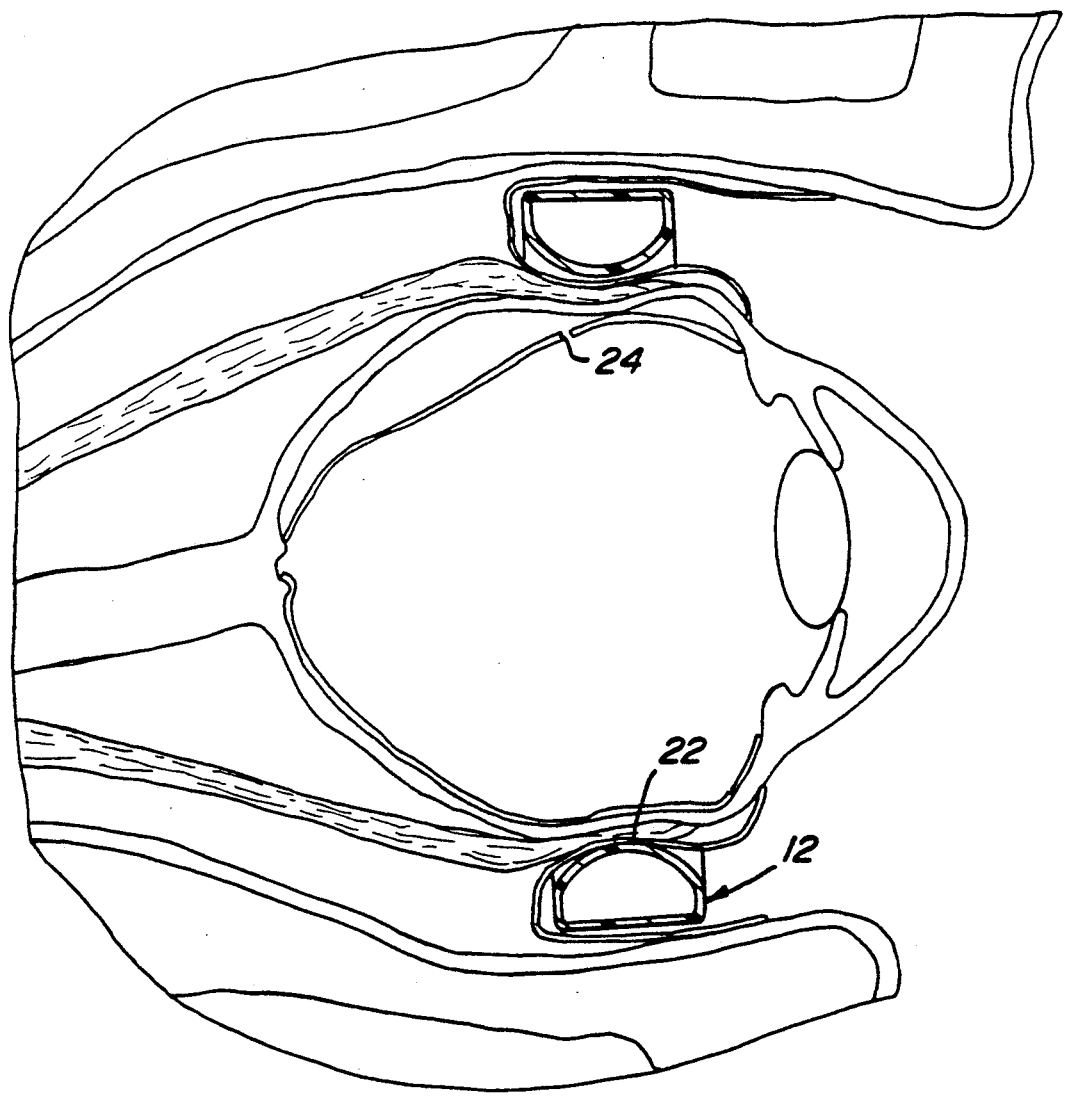
FIG. 7 is a cross sectional view showing the expanded tubular portion of the present invention indenting the eye.

The tubular member is inflatable for creating a gripping contact between a centripetally inwardly facing surface thereof 22 and the forniceal bulbar conjunctival surface of an eye when the device is disposed thereabout, as shown in FIGS. 6 and 7. Pressure is applied by the tubular member 12 to the conjunctival surface by at least a portion of the innersurface 22 which inflates radially inwardly for indenting the eye.

The tubular member is shown in FIG. 3,4 and 5 as progressively inflating in each of the Figures. FIG. 3 shows the tubular member in the deflated condition as a substantially ring-shaped member having a flat cross sectional appearance. FIG. 4 shows the tubular member partially inflated wherein the entire radially inwardly facing surface expands radially inwardly. FIG. 5 shows the tubular member with the radially inwardly facing surface fully inflated.

As shown in FIGS. 6 and 7, the radially inward expansion of the tubular member forces that surface against the bulbar conjunctival surface. In this embodiment, the entire inwardly facing surface 22 of the tubular member 12 not only grips the conjunctival surface, but also produces an indentation about a 360° circumference of the globe. Alternatively, the tubular member can be made with selected portions of the inwardly facing surface thereof being more inflatable than other portions so as to project radially inwardly more than the remainder of the inwardly facing surface. In this manner, this inwardly projecting surface which projects radially inwardly to a greater degree than the remainder of the radially inwardly facing surface will selectively indent a predetermined portion of the globe directly adjacent thereto when the tubular member 12 is disposed at a preselected position. Hence, the present invention can be used to indent either a selected portion of the globe, such as where there is a retinal tear, as shown schematically at 24 in FIGS. 6 and 7 or it can be used to produce an entire circumferential indentation. Utilizing the device including an inwardly projecting portion of the inwardly facing surface 22 of the tubular member 12, the remaining inwardly facing surface of the tubular member which inflates inwardly to a lesser degree still provides the gripping contact between the tubular member 12 and the bulbar conjunctival surface while the radially inwardly facing surface portion which extends inwardly to a greater degree specifically indents a predetermined portion of the globe.

A connector member 20 is shown in FIG. 2 which connects a tubular member 12 in fluid contact with the fluid conducting conduit 16. In this embodiment, the connector member 20 is a T-shaped member. The tubular member could be an extruded tube having ends 26, 28 in frictional sealed (or other types of) engagement with arms 30 and 32 of the connector 20, respectively. The conduit 16 includes an end portion 34 in frictional sealed (or other types of) engagement neck portion 36 of the connector member 20. The connector member 20 can include a valve such as leaf valve 38 which allows only one way fluid flow from the conduit 16 into the tubular member 12. Of course, the connector member 20 can take on many different forms including various means for connecting the ends 26, 28 of the tube member 12 thereto as well as various other valve constructions for allowing either one way or two way fluid flow therethrough. Of course, the connector member 20 may not even include a valve but rather the flow of fluid could be controlled by means exterior to the connector member 20.

The device 10 includes a fluid pump 14 and conduit 16 for fluid communication between the pump 14 and the tubular member 12, thereby conveying fluid therebetween. The pump can be of the type for pumping either a liquid, such as water or saline solution or a gas such as air or nitrogen to the tubular member 12. Pumps such as a Harvard pump, motor driven peristaltic pump, or other types of pumps can be utilized to provide precisely defined fluid flow control from a fluid reservoir, schematically shown at 40 to the tubular member 12.

The invention includes means for controlling the flow of fluid into and out of the tubular member 12 and from the pump mechanism 14. For example, the mechanism can include a pressure sensing apparatus schematically shown at 42 which is in electronic communication with a microprocessor 44, control pad 46, motor controller 48, servo motor 50, and feed back to the metering pump 14. In this embodiment, pressure is controlled as the servo motor raises or lowers the height of the fluid reservoir 40 thereby effecting changes in fluid pressure in response to pressure sensed by the pressure transducer 42. There are alternative means to be utilized to adjust fluid pressure in response to sensed pressure in the system well known in the art. Alternatively, volume of fluid flow can be controlled as discussed below.

The pump mechanism 14 is designed to provide precision controlled volumetric insufflation of the tubular member 12. As discussed above, the pump mechanism, or an external mechanism, is connected to the pressure sensing device 42 attached to the conduit 16 or directly sensing intraocular pressure by other means known in the art and displays the information on a front panel monitor, not shown in the Figures. The pressure sensing apparatus also serves as a feedback loop and adjusts the rate of filling of the tubular member 12 to a preset pressure or volume based upon the value of the intraocular pressure at specified time intervals. The pump 14 is designed to stop or reverse fill the inflatable tubular member 12 in the event that the measured intraocular pressure reaches or exceeds a pre-specified value, respectively.

In use, as for example in the corrective procedure for reattachment of a retinal detachment, as is illustrated in FIG. 6 and 7, when the tubular member 12 is inflated to a pre-specified volume or pressure, with the rate of filling preprogrammed and/or automatically adjusted to the discontinuously measured intraocular pressure, indentation of the sclera and choroidal coats beneath a torn or detached retina, as shown at 24, is estimated by the surgeon by fundus ophthalmoscopy. If the indentation is judged appropriate to affect closure of all retinal breaks and resorption of all subretinal fluid over time, the tubular conduit 16 attached to both the pump 14 and inflated tubular member 12 is disconnected from the connecter member 20. Valve 38 maintains the fluid pressure within the inflatable tubular member 12 by preventing any release of fluid therefrom.

In the event that the configuration of the ocular coat indentation is appropriate but the height inadequate, additional volume or pressure is added by the technique previously described. In the event that the configuration does not appear appropriate to the surgeon to sufficiently close the retinal break and effect subretinal fluid reabsorption, the inflatable tubular member 12 is deflated and either repositioned or replaced with another similar inflatable tubular member with a different surface configuration more appropriate to the detachment at hand.

A thermal chorioretinal adhesion is applied to visible retinal tears with laser photocoagulation following resolution of the subretinal fluid by a slit lamp or indirect ophthalmoscope delivery system or by other means known in the art. In some instances, including those where multiple breaks are present, where no breaks are seen, or where extensive subretinal fluid is present, the surgeon may wish to apply laser as a continuous double or triple row to the anterior retinal periphery over 360°. In certain other circumstances, such as those in which there is little or no subretinal fluid beneath the retinal tear itself, the surgeon may elect to treat the tear with laser or cryo therapy prior to application of the inflatable catheter to induce a sealing chorioretinal adhesion.

After an appropriate length of time determined by the surgeon during which the retina has been fully reattached and chorioretinal adhesion matured to an appropriate degree to effect long term retinal reattachment (approximately one to two weeks), the inflatable catheter is deflated and removed and the procedure completed.

For other procedures, such as vitrectomies, it may be desired to indent the eye such that corrective surgery can be accomplished. In these circumstances, the tubular member can be disposed about the globe and inflated for a much shorter period of time, such as a fraction of one hour to a few hours. Thusly, the present invention can be used to produce scleral and choroidal indentation during a vitrectomy thereby freeing one of the surgeons hands which would otherwise be required to hold a device for indenting the globe.

Immediately prior to the performance of cataract extraction and intraocular lens implantation, a number of preparatory maneuvers are undertaken to faciltate the surgical procedure and minimize the risk of intraoperative and postoperative complications. These steps include such as dilation of the pupil with pharmacologic agents to improve visualization, administration of anesthesia to prevent pain an dpatient non-compliance, and sterilization of the eye to prevent postoperative infection. A more recent innovation has been the indroduction of techniques to reduce the introcular pressure immediately prior to the surgical incision to lessen the possibility of unplanned loss of vitreious gel from the posterior segment of the eye and the catastrophic complication of expulsive choroidal hemorrhage.

The intraocular pressure can be reduced by both pharmacologic and mechanical means. Pharmacologic methods include the administration of carbonic anhydrase inhibitors such as acetazolamide (diamox) which reduce aqueous secretion in the yey, or hyperosmotic agents such as glycerol, mannitol, or urea which result in the relative dehydration of aqueous component of the vitreous body. Pharmacologic methods of intraocular pressure reduction have generally fallen out of favor because of their unpredictability and potential systemic complications and have been replaced by mechanical methods. (8).

Figure 8:
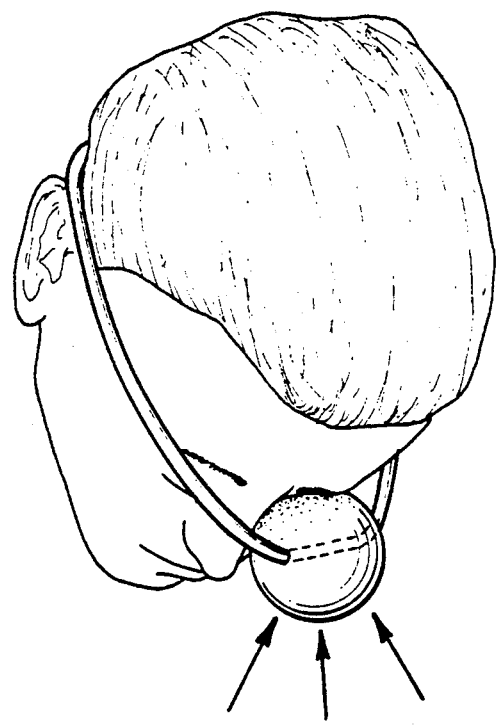
FIG. 8 shows a prior art method of ocluar decompression.

Mechanical methods consist of the application of force to the anterior surface of the globe, generally through the closed lid which has the effect of reducing the introcular pressure. This may be achieved by digital massage, application of a soft elastic ball to the lid, or inflation of a bag, analogous to a blood pressure cuff (9,10). These devices are intimately apposed to the globe at a preset tension which is judged not likely to produce a retinal or choroidal vascular occlusion. (FIG. 8). The precise mechanism by which the intraocular pressure is reduced and the globe consequently softened remains somewhat controversial. Some authors believe that the principal effect of the compression is a temporary reduction in orbital volume which consequently transmits less pressure to the surface of the eye. (9) Others feel that the application of force to the globe results in egress of portions of the aqueous humor thorough the drainage angle, and the aqueous portions of the bitreous body through other cannels. The rate of this aqueous outflow is proportional to the instataneous introcular pressure through a constant termed the coefficient of outflow which varies slightly from eye to eye. This variability in the coefficient of outflow from eye to eye is in part responsible for the theoretical reisk of excessively elevated introcular pressure or vascular compromise since introcular pressures are not able to be routinely measured during these mechanical techniques.1

Immediately prior to cataract surgery, the device made in accordance with the present invention can be disposed about the globe to produce softening of the eye (a transient decrease in intraocular pressure). Thusly, the surgeon can attempt to reduce the possibility of vitreous expulsion or choroidal hemorrhage due to increase intraocular pressure in the cataract patient.

The potential advantages with regard to ocular decompression immediately prior to cataract extraction by the device described in this patent application are several fold. (1) Pressure is applied directly to the globe rather than to the lids which results in a more uniform application of force. (2) No pressure is applied over the cornea (through the eyelid) which reduces the likelihood of corneal swelling or deformation. (3) The introcular pressure is measured directly and determines the rate of compression; hence the risk of excessive transient introcular pressure elevation and attendant vascular compromise are lessened. A potential disadvantage of this technique is that little if any decompression of orbital contents is achieved, although the significance of this is not clear.

Accordingly, the present invention provides a method of indenting the scleral and choroidal coats of an eye by gripping the eye about the bulbar conjunctival surface and applying a pressure about at least a portion of the forniceal conjunctival surface to indent the eye. The gripping step is achieved by surrounding the eye with the inflatable tubular member 12 within the fornices of the eye socket. The pressure applying step is achieved by inflating at least a portion of the tubular member 12 radially inwardly against the forniceal conjunctival surface to indent the eye.

The device and technique described differ significantly from all previous methods. This procedure can be performed without any ocular perforation or incision; therefore, the threat of either intraocular bleeding, infection, or scarring is negligible. This is not the case for all previously described methods. Because this device is applied to the outside of the eye, it may be subject to different regulations and restrictions than implanted materials and less prone to later complications such as scarring, infection, extrusion, migration or ocular motor disturbance. Because the device is applied to the eye and no incisions or sutures required, lesser degrees of anesthesia and/or sedation may be required. For the same reasons, the procedure may be performed in an office or outpatient setting under clean but not necessarily sterile conditions resulting in potential cost savings to both the patient and surgeon. Because the size of the inflatable catheter is determined by incremental inflation of a fluid regulated by feedback from an intraocular pressure sensing device, patient discomfort, intraocular pressure elevation, and vascular compromise can be minimized. In those instances in which retinal reattachment cannot be achieved by the above methods, the prospects for retinal reattachment by other conventional methods such as intraocular gas injection, or surgical scleral buckling and/or vitrectomy are not unduly prejudiced.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. A method of indenting the ocular coats of an eye, said method including the steps of: gripping the eye about the intra-forniceal bulbar conjunctival surface by surrounding the eye with an inflatable tubular member within the fornices of an eye socket, and applying a pressure about at least a portion of the bulbar conjunctival surface to indent the eye by inflating at at least a portion of the tubular member centripetally (inwardly) against the forniceal conjunctival surface to indent the eye.

2. A method as set forth in claim 1 further including the steps of indenting the ocular coat of an area including retinal breaks, closing the retinal breaks, closing the retinal breaks, reabsorbing subretinal fluid, and creating an adhesion between the retina and underlying pigment epithelium.

3. A method as set forth in claim 2 wherein the tubular member is an inflatable ring-shape balloon including a centripetally (inwardly) projecting inflatable portion, said method further including the steps of disposing the balloon about the eye, positioning the inflatable projecting portion at a predetermined position and inflating the balloon to retain the balloon about the eye while the inflating projecting portion applies pressure to the forniceal conjunctival surface and indents the ocular coat.

4. A method as set forth in claim 1 further including the steps of controlling the amount of inflation of the balloon while detecting changes in intraocular pressure.

5. A method as set forth in claim 4 wherein said inflating step is further defined as inflating the balloon with a fluid.

6. A method as set forth in claim 5 wherein said controlling step is further defined as measuring the volume of fluid insufflation.

7. A method as set forth in claim 6 wherein said measuring step is based on the measured value of intraocular pressure at preset time intervals.

8. A method as set forth in claim 5 wherein said controlling step is further defined as measuring the pressure of fluid insufflation.

9. A method as set forth in claim 8 wherein said measuring step is based on the measured value of intraocular pressure at preset time intervals.

10. A method as set forth in claim 1 further including the steps of transiently applying the pressure for up to six hours and removing the tubular member.

11. A method as set forth in claim 1 further including the step of maintaining the pressure for up to four weeks.

12. A method as set forth in claim 10 or 11 wherein said removing step is further defined as deflating the tubular member and removing the tubular member from the forniceal space.

13. A method as set forth in claim 1 further including the step of softening the eye by decreasing the intraocular pressure of the eye.

14. A method as set forth in claim 13 further including the step of removing the tubular member by forcing the inflated tubular member off of the softened eye.

* * * * *